(12) United States Patent
Takahashi (10) Patent No.: US 7,651,656 B2
(45) Date of Patent: Jan. 26, 2010

(54) MELTING FURNACE WITH AGITATOR AND AGITATOR FOR MELTING FURNACE

(76) Inventor: Kenzo Takahashi, 149, Rokkodai 9-Chome, Matsudo-Shi, Chiba-Ken (JP)

( * ) Notice: Subject to any disclaimer, the term of this patent is extended or adjusted under 35 U.S.C. 154(b) by 200 days.

(21) Appl. No.: 11/658,991

(22) PCT Filed: Jul. 20, 2006

(86) PCT No.: PCT/JP2006/314425

§ 371 (c)(1), (2), (4) Date: Jan. 31, 2007

(87) PCT Pub. No.: WO2008/010285

PCT Pub. Date: Jan. 24, 2008

(65) Prior Publication Data

US 2009/0020925 A1 Jan. 22, 2009

(51) Int. Cl.
*C21C 7/00* (2006.01)
(52) U.S. Cl. .................................... 266/234
(58) Field of Classification Search .............. 266/233, 266/234
See application file for complete search history.

(56) References Cited

U.S. PATENT DOCUMENTS 3,547,622 A * 12/1970 Hutchinson ................. 266/234
4,336,411 A   6/1982 Hanas et al. .................. 373/85
4,778,518 A * 10/1988 Bergman et al. ............. 266/234
4,867,786 A *  9/1989 Saeki et al. .................. 266/234
6,026,113 A   2/2000 Pavlicevic et al. ............. 373/85

FOREIGN PATENT DOCUMENTS

| JP | 54-161506 | 12/1979 |
| JP | 56-138671 | 10/1981 |
| JP | 03-187923 | 8/1991 |
| JP | 06-201266 | 7/1994 |

OTHER PUBLICATIONS

International Search Report from International Application No. PCT/JP2006/314425, mailed Oct. 17, 2006.
Translation of PCT International Preliminary Report on Patentability in counterpart International application No. PCT/JP2006/314425, dated Jan. 29, 2009.
Office Action in counterpart Canadian Application No. 2,578,691, dated Mar. 5, 2009.

* cited by examiner

*Primary Examiner*—Scott Kastler
(74) *Attorney, Agent, or Firm*—Winston & Strawn LLP (57) ABSTRACT

There are provided a melting furnace including a containing space for containing a melt of nonferrous metal, a magnetic field generating device, a magnetic flux therefrom, from outside penetrates the melting furnace for containing the melt to run through the containing space in a direction; and at least one pair of electrode terminals, the electrode terminals facing each other with a predetermined distance in a direction crossing the direction of the magnetic flux at a certain angle, and being capable of connecting to a power supply.

14 Claims, 8 Drawing Sheets

MELTING FURNACE WITH AGITATOR AND AGITATOR FOR MELTING FURNACE

BACKGROUND OF THE INVENTION

1. Field of the Invention

The present invention relates to a melting furnace with an agitator and an agitator for a melting furnace.

2. Background Art

Conventionally, nonferrous metals and so on, such as aluminum, etc., are melted to form ingot products, or melted and directly cast by a die casting machine to manufacture products. On such an occasion, in order to homogenize a nonferrous metal or the like to improve the quality of ingot products or die cast products, the melt of the nonferrous metal in the melting furnace, i.e., Al, Cu, Zn or an alloy of at least two of them, or a nonferrous metal such as an Mg alloy is fully stirred to homogenize the components. As the result, conventionally, an agitator is inserted in the melting furnace to agitate the melt by manpower, or the furnace is sealed and a negative pressure and a positive pressure are alternately applied to agitate the melt, or an electromagnet type agitator or a permanent magnet type agitator is provided under the furnace bottom to agitate the melt by electromagnetic force. The agitation by manpower is often employed, but since the work should be performed under a high temperature and the working environment is very severe, the improvement of the working conditions is demanded. The electromagnetic agitation is not widely used since it requires a large amount of power consumption, complicated maintenance works, and a high cost. Although the power consumption required in the permanent magnet type apparatus is low, it is necessary to rotate a magnetic field generating mechanism for generating a shifting magnetic field, which complicates the structure of the apparatus, and causes failures at a rate which is not low.

SUMMARY OF THE INVENTION

As described above, it is necessary to operate the apparatus under the severe work environment conditions. Of course, the conditions are severe for not only the apparatus but also the workers. Accordingly, it is desirable that the apparatus have an as-simple-as-possible structure and be maintenance-free. Furthermore, it is desirable that the apparatus be an agitator consuming low power, being easy to install, and being cheap and easy to be widely spread.

It is an object of the present invention to provide such an apparatus.

The present invention is characterized by including a melting furnace including a containing space for containing a melt of nonferrous metal, a magnetic field generating device for causing a magnetic flux to penetrate, from outside, the melting furnace for containing the melt so as to run through the containing space in a direction, and at least one pair of electrode terminals, the electrode terminals facing each other with a predetermined distance in a direction crossing the direction of the magnetic flux at a certain angle, and being capable of connecting to a power supply.

Furthermore, the present invention is characterized by including a magnetic field generating device, a magnetic flux therefrom, from outside penetrates the melting furnace including a containing space for containing a melt of nonferrous metal to run through the containing space in a direction; and at least one pair of electrode terminals, the electrode terminals facing each other with a predetermined distance in a direction crossing the direction of the magnetic flux at a certain angle, and being capable of connecting to a power supply.

Moreover, the present invention is characterized by including a melting furnace including a containing space for containing a melt of nonferrous metal, a magnetic field generating device for causing a magnetic flux to penetrate, from outside, the melting furnace including a containing space for containing a melt of nonferrous metal to run through the containing space in a direction, and at least one pair of electrode terminals each being capable of connecting to a power supply, the electrode terminals being provided with a predetermined distance therebetween, one of the electrode terminals constituting the pair being provided to a position corresponding to the magnetic field generating device, and the other being provided to an arbitrary position.

Further, the present invention is characterized by including a magnetic field generating device for causing a magnetic flux to penetrate, from outside, the melting furnace including a containing space for containing a melt of nonferrous metal to run through the containing space in a direction, and at least one pair of electrode terminals each being capable of connecting to a power supply, the electrode terminals being provided with a predetermined distance therebetween, one of the electrode terminals constituting the pair being provided to a position corresponding to the magnetic field generating device, and the other being provided to an arbitrary position.

DESCRIPTION OF THE EMBODIMENTS

Figure 1:
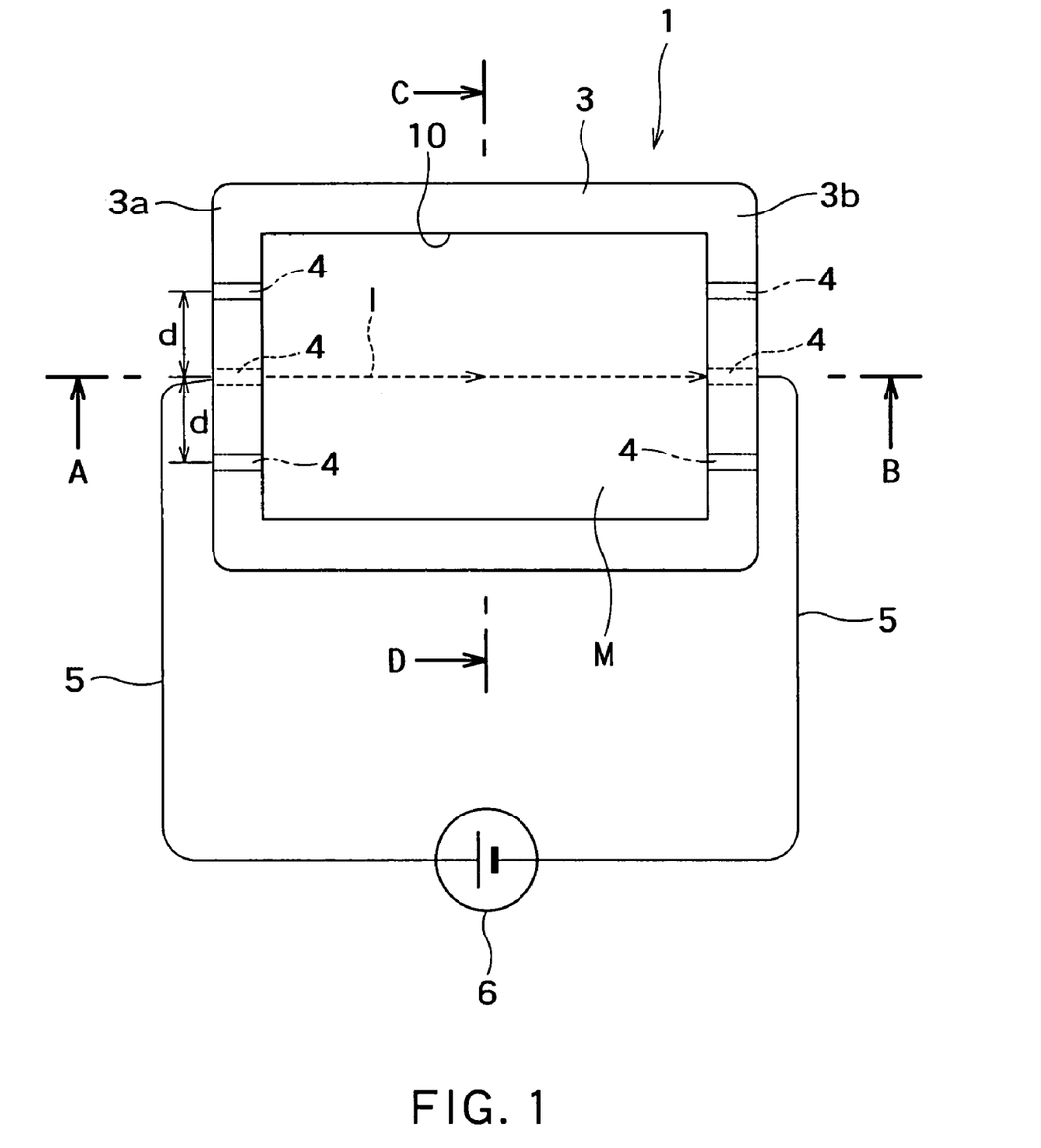
FIG. 1 is a plan view of an embodiment of the present invention.
Figure 2:
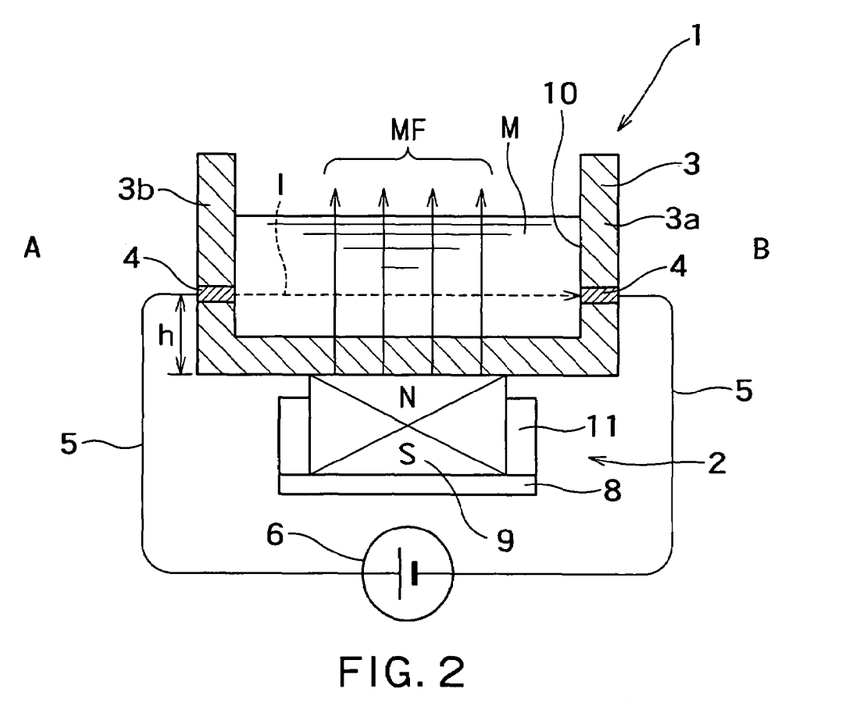
FIG. 2 is a sectional view taken along line A-B of FIG. 1.
Figure 3:
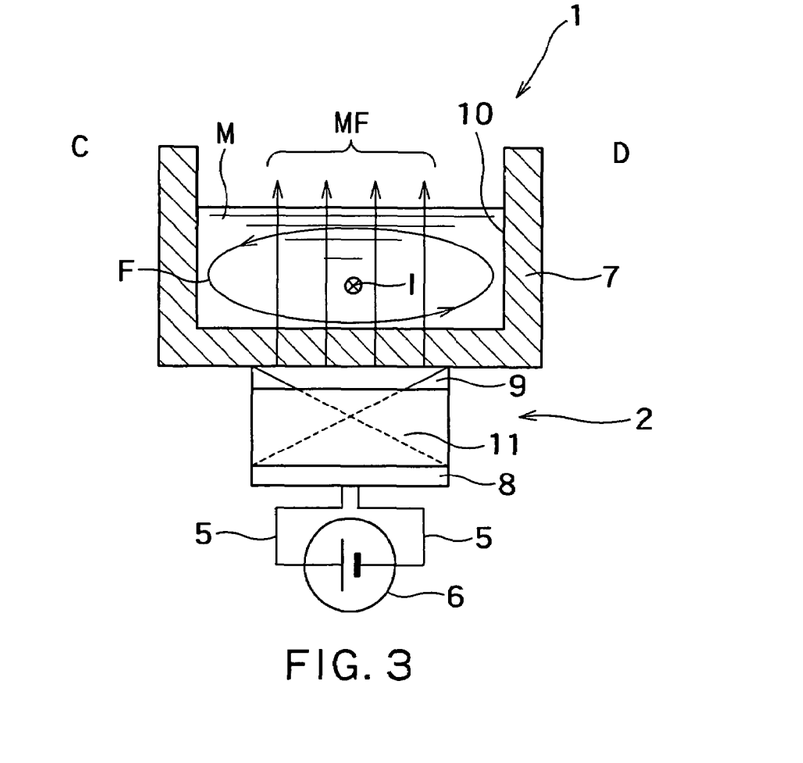
FIG. 3 is a sectional view taken along line C-D of FIG. 1.

FIGS. 1 to 3 show a melting furnace system, i.e., a melting furnace with an agitator according to an embodiment of the present invention. FIG. 1 is a plan view, FIG. 2 is a sectional view taken along line A-B in FIG. 1, and FIG. 3 is a sectional view taken along line C-D in FIG. 1.

Conceptually, the melting furnace with an agitator includes a melting furnace, a magnetic field generating device, and a power feeding device. In the embodiment, as is clear especially from FIG. 2, a melting furnace with an agitator includes a melting furnace 1 and an agitator 2 serving as the magnetic field generating device mounted on the bottom of the melting furnace 1 in a contacting state. Furthermore, the melting furnace 1 includes electrodes (electrode terminals) 4, 4 serving as the power feeding device. Naturally, these electrodes 4, 4 are connected to a power supply 6. The power supply 6 can constitute a part of the power feeding device. Alternatively, the power supply 6 can be an external power supply that is not included in the power feeding device.

The melting furnace 1 includes a melt containing space 10 for melting a nonferrous metal poured thereinto, i.e., Al, Cu, Zn, or an alloy of at least two of them, or an alloy of a conductive (electrically conductive) nonferrous metal such as an Mg alloy with a burner etc. not shown in the drawing in the same manner as in a generally-used melting furnace. The melting furnace 1 includes a furnace main body 3 of a substantially rectangular container shape. As can be understood especially from FIG. 2, the furnace main body 3 has a pair of electrode 4, 4 embedded in a sealing and penetrating manner in a pair of facing sidewalls (furnace sidewalls) 3a, 3b. These electrodes 4, 4 can be embedded at the time of the manufacture of the furnace main body 3 or can be embedded in an already manufactured furnace main body 3 later. The cross-sectional shape of the electrodes 4, 4 can be circular, rectangular, or a desired shape. The inside ends of the electrodes 4, 4 are exposed so as to be flush with the internal surfaces of the furnace main body 3 to electrically contact the melt M contained in the furnace main body 3, the melt M being Al, Cu, or Zn or an alloy of at least two of them, or a conductive (electrically conductive) nonferrous metal such as an Mg alloy. The electrodes 4, 4 are flush with the internal surfaces of the furnace main body 3 so as to prevent the electrodes 4, 4 from becoming mechanical resistance against the movement of the melt, which will be described later, in the furnace main body 3. Of course, if the mechanical resistance is small, the electrodes 4, 4 can project toward the inside of the furnace main body 3.

The electrodes 4, 4 are connected to the aforementioned power supply 6 outside the furnace with a cable 5, 5. As a result, for example in FIG. 2, a current I flows between the electrodes 4, 4 from the left side to the light side through the melt M of a nonferrous metal serving as a conductive body. As described above, the power supply 6 can be included in the power feeding device or can be an external power supply. Furthermore, it is possible to configure the power supply 6 so that the polarity thereof can be switched. That is to say, for example in FIG. 2, the current I can be arranged to flow from the left side to the right side as shown in the drawing, or can be switched to flow from the right side to the left side. Moreover, it is possible to constitute the power supply 6 so that the outputs thereof, i.e., the output voltage and the output current thereof, can be adjusted.

As can be understood form FIG. 1, two pairs or more of electrodes can be provided. The most important thing is to cause a current to flow from the left side to the right side and vice versa in FIG. 1. For example, as can be understood from FIG. 1, if three pairs of electrodes are provided, the distance d between adjacent pairs does not become a problem.

As can be understood especially from FIG. 2, an agitator 2 is provided in a contacting manner at the bottom of the melting furnace 1 thus constituted. The agitator 2 has a magnetic field device (magnetic field generating device) 9 mounted on a yoke 8. The magnetic field device 9 is fixed, and it is not necessary to make it rotatable. Accordingly, the possibility of the occurrence of failure is curbed, and this apparatus is easy to use from the viewpoint of maintenance. The magnetic field device 2 can be of a permanent magnet type or an electromagnet type. The electrode can be of circular or rectangular. The magnetic flux MF from the magnetic field device 9 penetrates the bottom portion of the furnace main body 3 substantially perpendicularly, and the direction thereof is not important. FIG. 2 shows an example in which the side of the magnetic field device 9 near the bottom of the furnace main body 3 is the north pole side, and the magnetic flux from the magnetic field device 9 penetrates the bottom and pass through the melt M in the furnace main body 3. On the contrary, it is possible to constitute the magnetic field device 9 so that the side thereof near the bottom of the furnace main body 3 is the south pole side, and the magnetic flux MF penetrating the melt M and the bottom of the furnace main body 3 returns to the south pole.

Furthermore, in the case where the magnetic field device 9 is of an electromagnet type, it is possible to adjust it by switching the polarity and the intensity thereof. That is to say, it is possible to constitute the magnetic field device 9 so that the north pole and the south pole are switchable, and the output thereof can be increased or decreased, i.e., so as to have an output adjustment function.

The magnetic field device 9 is surrounded by a stainless case 11. As mentioned before, the magnetic flux MF from the magnetic field device 9 is generated so as to penetrate the melt M substantially perpendicularly from the bottom side to the top side, as shown in FIG. 2.

In the system thus constituted, as can be particularly understood from FIG. 2, a current I flows between a pair of electrodes 4, 4 in the magnetic field space. As a result, the melt M is rotated by the electromagnetic force in accordance with Fleming's left hand rule. Specifically, the melt M is rotated by the repulsive force generated due to the current I as shown in FIG. 3. That is to say, for example in FIG. 2, the magnetic flux MF from the magnetic field device 9 penetrates the melt M upwardly. On the other hand, the current I flows between the pair of electrodes 4, 4 through the melt M. In FIG. 3, the current I is shown to flow from the front paper surface side to the back paper surface side. Thus, the magnetic flux MF runs through the conductive melt M, and the current I flows therethrough. As a result, in accordance with Fleming's left hand rule, an electromagnetic force is generated, by which the melt M is pressed to move toward the outside of the magnetic field, resulting in that the melt M is stirred in a rotatable state as shown by the flow of melt F in FIG. 3. That is to say, the melt M is circulated from the furnace bottom to the melt surface, and from the melt surface to the furnace bottom by the repulsive force working between the melt M and the current I, thereby being agitated up and down.

In this state, if the direction of the current flowing through the pair of electrodes 4, 4 is changed, or the direction of the magnetic flux from the magnetic field device 9 is changed, it is possible to reverse the direction of agitating the melt M. Furthermore, this agitation is not intermittent but continuous.

It is obvious that the height h of the electrodes 4, 4 in FIG. 2 is required to allow the current I flowing between the electrodes 4, 4 to flow in the magnetic field space generated by the magnetic field device 9.

Figure 4:
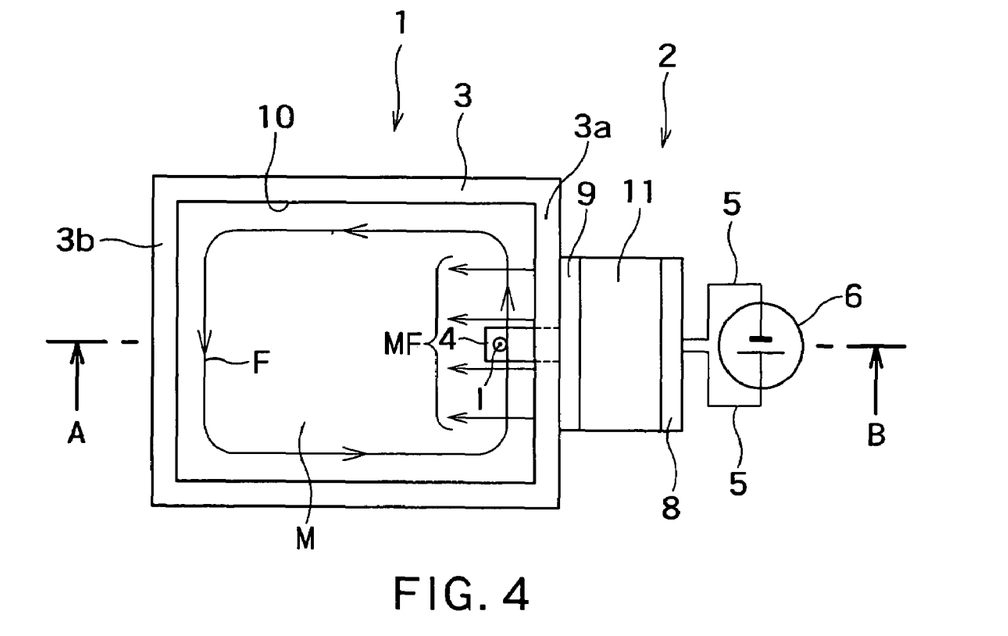
FIG. 4 is a plan view of another embodiment of the present invention.
Figure 5:
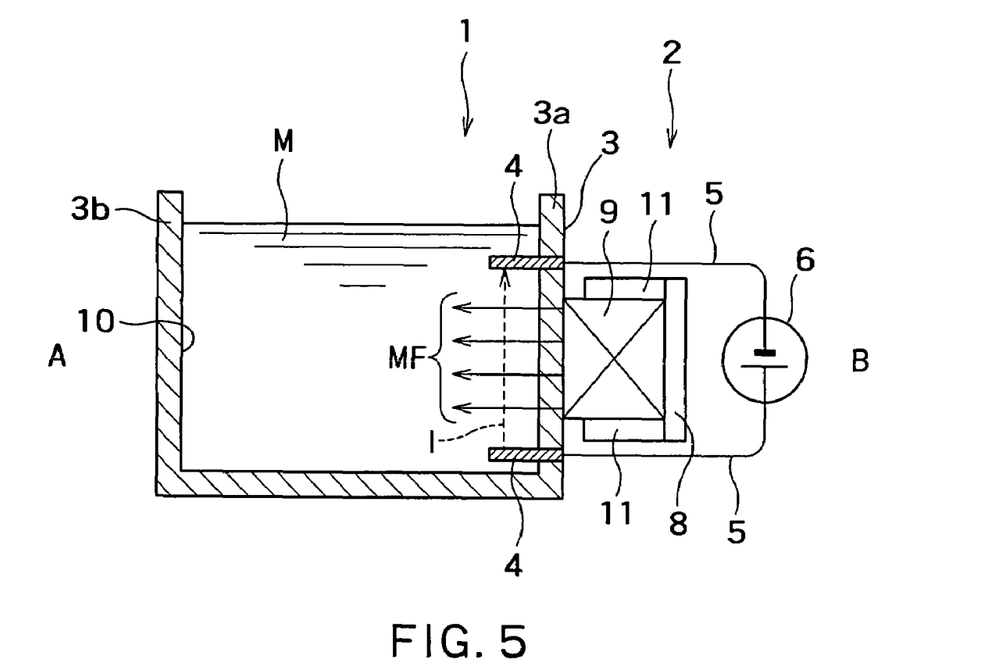
FIG. 5 is a sectional view taken along line A-B of FIG. 4.

FIGS. 4 and 5 show another embodiment of the present invention. FIG. 4 is a plan view, FIG. 5 is a sectional view taken along line A-B in FIG. 4. As can be understood in particular from FIG. 5, this embodiment shows an example in which an agitator 2 is provided in a contacting manner at the outside of a sidewall 3a of a melting furnace 1.

Specifically, a pair of electrodes 4, 4 is embedded in a sealing manner at an upper portion and a lower portion in one of the sidewalls 3a of the furnace main body 3 so that the electrodes have a predetermined distance therebetween. The inside ends of the electrodes 4, 4 project toward the inside of the furnace main body 3 so as to have a distance from the internal surface of the furnace main body 3.

In this case, as shown in FIG. 5, a current I flows through the melt M along the sidewall 3a and with a slight distance from the sidewall 3a. As in the case of the previously described embodiment, a magnetic flux MF from the magnetic field device 9 passes through the melt M as shown, in particular, in FIG. 4. As can be understood from FIG. 4, an electromagnetic force is generated in accordance with Fleming's left hand rule based on the current I and the magnetic flux MF. The melt M is rotated around the current I by the electromagnetic force, as shown in FIG. 4. That is to say, the melt M is rotated around a substantially perpendicular axis. Thus, the melt is horizontally stirred.

With reference to FIGS. 4 and 5, an example of providing the electrodes 4, 4 at the furnace wall of the furnace main body 3 has been described. The electrodes 4, 4 can be positioned at desired upper and lower facing positions on the internal surface within the melt containing space 10 in an area where the current I from the magnetic field device 9 flows through the magnetic field space. Furthermore, the number of the pairs of electrodes 4, 4 provided to the upper and lower positions can be decided arbitrarily.

Figure 6:
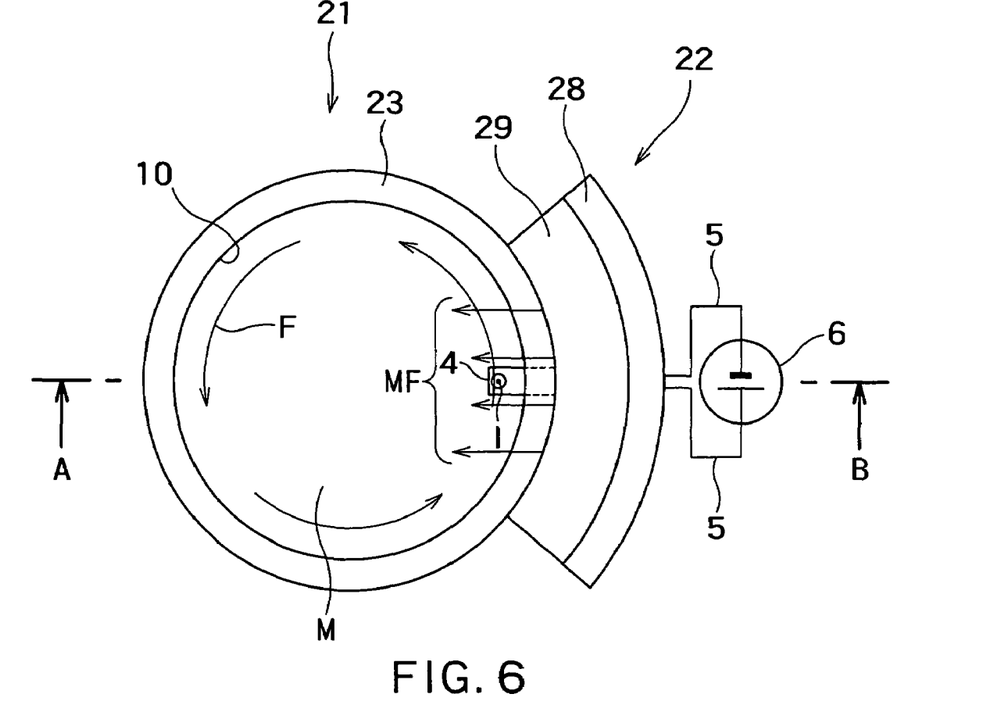
FIG. 6 is a plan view of a further embodiment of the present invention.
Figure 7:
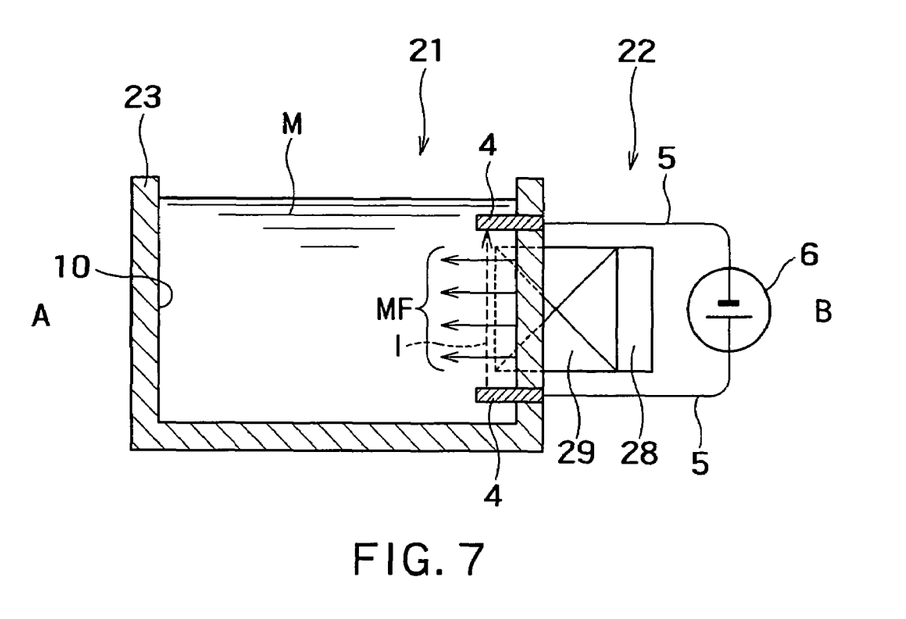
FIG. 7 is a sectional view taken along line A-B in FIG. 6.

FIGS. 6 and 7 show a further embodiment. FIG. 6 is a plan view, and FIG. 7 is a sectional view taken along ling A-B of FIG. 6. FIG. 6 corresponds to FIG. 4, and shows an example in which a furnace main body 23 has a substantially cylindrical container shape. That is to say, this embodiment can be seen as a modification of the embodiment shown in FIGS. 4 and 5. In other words, the shape of the furnace main body 3 of the melting furnace 1 is changed to a cylindrical container shape in the previous embodiment shown in FIGS. 4 and 5. That is to say, in this embodiment, the shape of the furnace main body 23 of a melting furnace 21 is a cylindrical container shape. So as to conform to this change, a yoke 28 and a magnetic field device 29 of an agitator 22 are curved to have arch shapes. The structure of the other portions of the embodiment shown in FIGS. 6 and 7 is the same as that of the embodiment shown in FIGS. 4 and 5. Accordingly, the same reference numerals are assigned to the common portions, and the descriptions thereof are omitted.

In the embodiment shown in FIGS. 6 and 7 thus constituted, the melt M is rotated around a substantially perpendicular axis and agitated as can be understood especially from FIG. 6, as in the case of the embodiment shown in FIGS. 4 and 5.

Even if the furnace main body 23 has a cylindrical container shape as shown in FIG. 6, it is possible to arrange the electrodes 4, 4 so as to face each other in a horizontal direction.

FIGS. 8 to 12 show a still further embodiment constituted based on a technical idea different from that of the aforementioned apparatuses. Specifically, the apparatuses of the aforementioned embodiments are suitable for rotating the melt at a relatively low speed. In contrast, the apparatus of the embodiment described below is suitable for rotating the melt at a speed a few tens times higher than the aforementioned apparatuses. The speed at which the melt is rotated is appropriately selected. That is to say, the agitation speed can be appropriately selected based on the objective such as to homogenize the components of the melt, to stabilize the temperature when the agitation is performed, to agitate with an excessive oxidation being prevented, and to consider the type of the metal serving as the melt material.

Furthermore, the embodiment described below is constituted considering the following points.
(1) The entire current flowing is concentrated in the magnetic field area in order to maximize the electromagnetic force to be obtained.
(2) The braking force (the force acting to stop the movement of the melt) caused by the eddy current generated within the melt moved by the magnetic field externally applied and the electromagnetic force is curbed as much as possible.

In the embodiment described below, the same reference numerals are assigned to the portions common to those in the previously described embodiments, and the detailed descriptions thereof are omitted.

Figure 8:
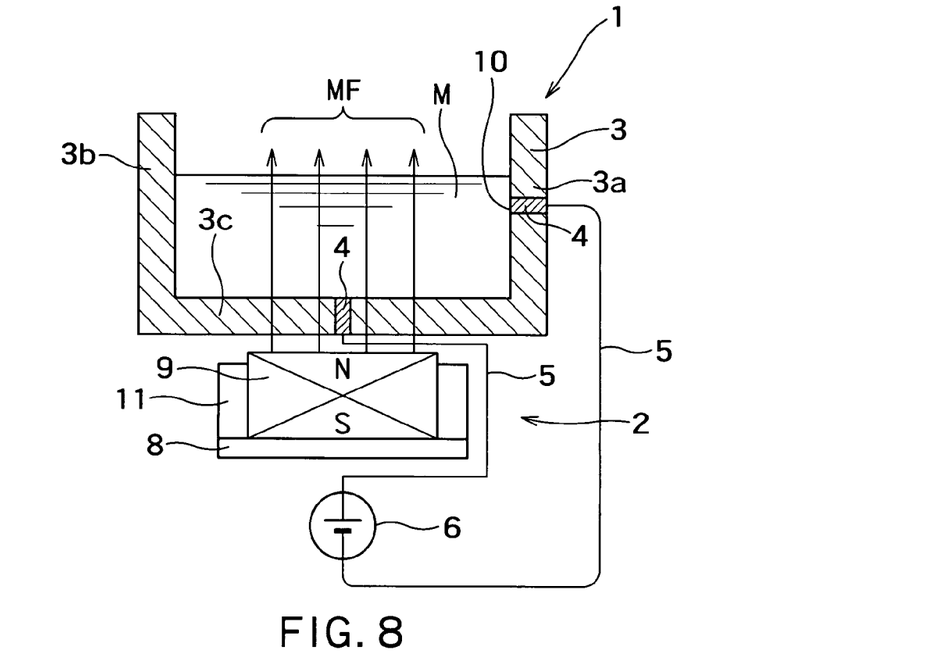
FIG. 8 is a sectional view of a still further embodiment of the present invention.

FIG. 8 is a schematic sectional view for explaining the principle of the embodiment described below.

The difference between the embodiment shown in FIG. 8 and the embodiment shown in FIG. 2 lies in that one of the electrodes 4, 4 constituting a pair is embedded in a bottom wall (furnace bottom) 3c of the furnace main body 3. It is also obvious that the electrode is not necessarily embedded.

In the embodiment thus constituted, a current flows between the electrodes 4, 4 constituting a pair by applying a voltage across the electrodes 4, 4. The path through which the current flows in the melt M between the electrodes 4, 4 constituting a pair is unclear. However, regardless of which path a current flows between the electrodes 4, 4 constituting a pair, since one of the electrodes 4, 4 constituting a pair is provided to the bottom wall 3c, the entire current efficiently flows through an area in which the magnetic field intensity is higher. As a result, a maximum amount of electromagnetic force can be obtained due to the interaction between the magnetic field and the current. Thus, the aforementioned (1) can be achieved.

Furthermore, as can be understood from FIG. 8, the magnetic field line (magnetic flux MF) from the magnetic field generating device (agitator) 2 penetrates the melt M via the bottom wall 3c. In this case, the magnetic field generating device 2 has a monopole structure. As a result, assuming that there is a plane parallel to the bottom wall 3c, the magnetic field intensity is substantially uniform in this plane. In this environment, it is assumed that the melt M is moved by the aforementioned electromagnetic force. In this case, the melt M forms a rotational flow F rotating around the electrode 4 embedded in the bottom wall 3c. At this time, since the magnetic field intensity is uniform as described above, no eddy current (braking force) is generated as the melt M moves. That is to say, the eddy current is generated when magnetic flux $\phi$ is changed relative to time t, and since the magnetic flux distribution is uniform in this case, no eddy current is generated. As a result, the agitation of the melt is performed very effectively. Thus, the aforementioned (2) can be achieved.

Figure 10:
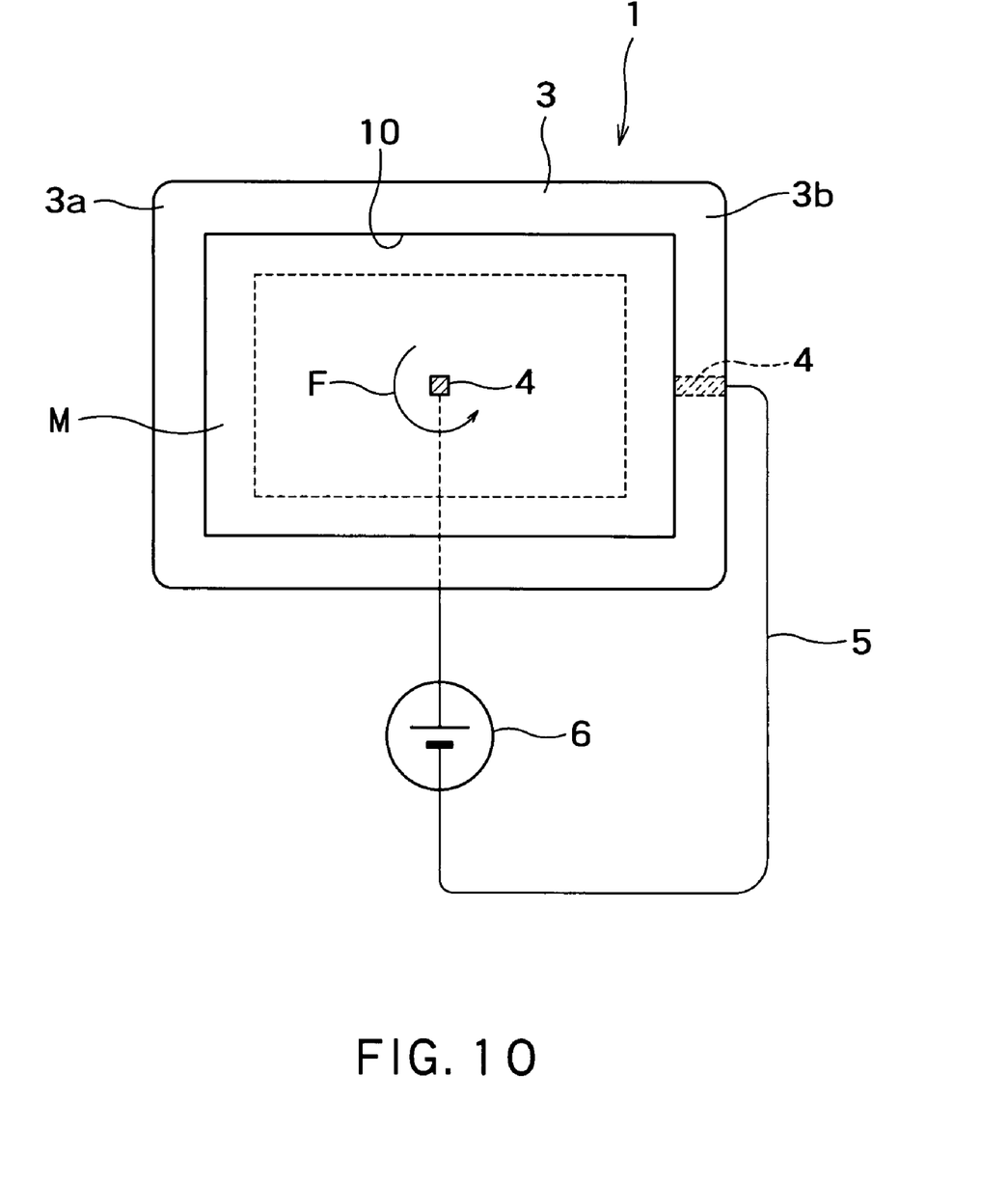
FIG. 10 is a plan view of the apparatus of the embodiment shown in FIG. 8.

FIG. 10 is a plan view of FIG. 8, and shows an embodiment in which the furnace main body 3 has a rectangular container shape.

Figure 9:
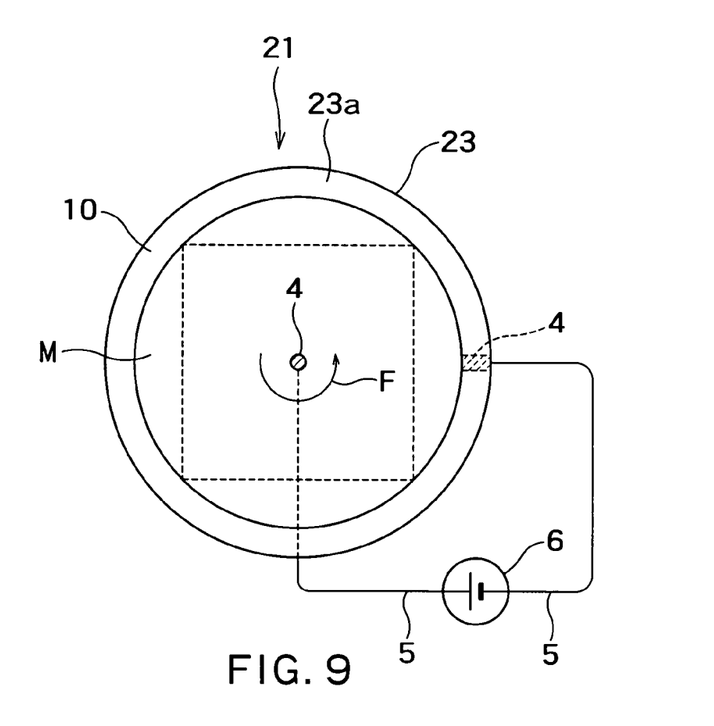
FIG. 9 is a plan view of an apparatus of an embodiment, for which the sectional view is substantially the same as that shown in FIG. 8.

FIG. 9 shows an embodiment of which the sectional view is substantially the same as that of FIG. 8. In this embodiment, the furnace main body 23 has a cylindrical container shape.

Furthermore, as a modification of the embodiments shown in FIGS. 8 to 10, it is possible to provide a desired number of electrodes at desired positions, besides the electrodes 4 provided to the sidewalls 23a and 3b and the bottom wall 3c.

Figure 11:
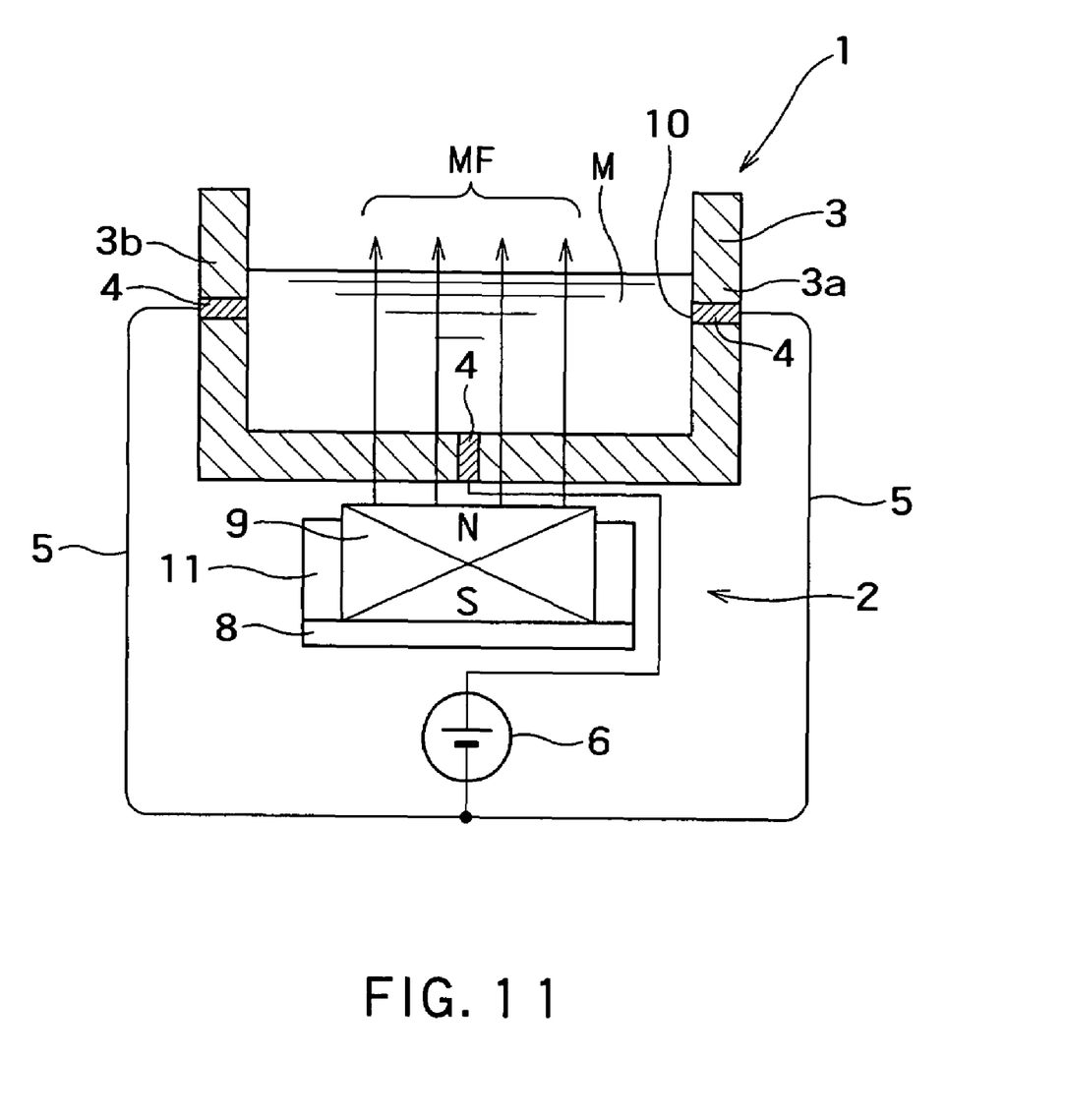
FIG. 11 is a sectional view of a yet further embodiment of the present invention.
Figure 12:
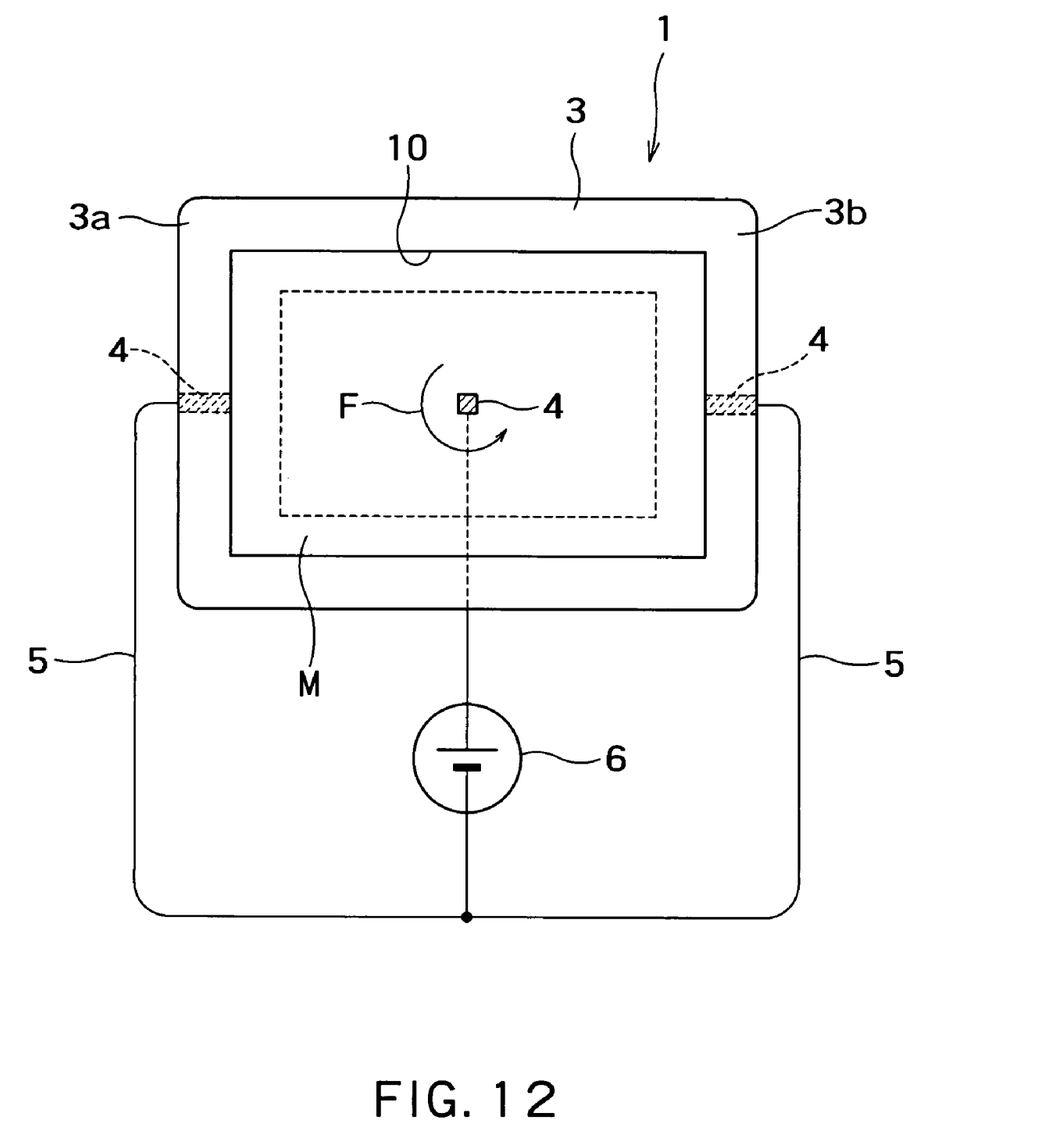
FIG. 12 is a plan view of the apparatus shown in FIG. 11.

For example, as modification of the embodiments shown in FIG. 8 and FIG. 10, it is possible to provide an electrode 4 to the sidewall 3a at the left side as shown in FIG. 11 and FIG. 12.

Furthermore, for example, although the electrodes 4, 4 are provided to the sidewalls 3a and 3b in the embodiment shown in FIG. 11 and FIG. 12, i.e., in total two electrodes 4, 4 are provided to the sidewalls 3a and 3b, it is obvious that the number of electrodes on the sidewalls 3a and 3b can be three or more.

Moreover, although one electrode 4 is provided to the bottom wall 3c in the embodiment shown in FIG. 11 and FIG. 12, it is possible to provide a plurality of electrodes 4 so as to correspond to the electrodes 4 provided to the sidewall 3a and 3b.

In the aforementioned embodiments, the section of the electrodes 4 can be of various shapes depending on the usage, the objective, etc. thereof. For example, circle, rectangle, or circular- or oval-ring shape can be employed.

The aforementioned embodiments only show some examples of the present invention, and it is obvious that there are other aspects of the present invention than those described above. That is to say, as long as an apparatus has a structure in which a melt is contained in a furnace main body, a magnetic flux is emitted within the melt from the outside of the furnace main body, and a current flows through the melt in a direction crossing the magnetic flux, such an apparatus is included within the spirit of the present invention.

According to the embodiments of the present invention described above, it is possible to obtain the following effects.

Generally, a melting furnace or holding furnace is often in a shape of a box. Circular shape furnaces are often used as melting auxiliary furnaces to which a material is poured to be rapidly melted. In many cases box-shaped furnaces agitate a melt slowly. In a case where components thereof should be adjusted, such as in the case of adding a metal element, it is required that the melt is agitated up and down. However, conventional type agitators could not agitate the melt up and down for the reason of structure. Since the melt is caused to move in a direction perpendicular to the electrodes by an agitator according to an embodiment of the present invention, it is possible to freely select the agitation direction and conditions by appropriately setting the electrode positions. Accordingly, it is possible to easily agitate a melt up and down or right and left, or to rotate a melt in a normal or reverse direction.

According to an experiment performed on an embodiment of the present invention, the applied magnetic field intensity required to agitate a melt is 0.1 T or more. Of course it is possible to perform agitation with the applied magnetic field intensity of 0.1 T or less. However, it is desirable that the applied magnetic field intensity is more than that in order to have a high agitation efficiency. Considering the principle thereof, it is not possible for an agitator according to the embodiments of the present invention to obtain the agitating force only from the magnetic field intensity. The magnitude of power consumption (applied voltage, supplied current) also greatly affects the agitating force. According to an experiment performed by the present inventor, about 500 kg of a melt can be agitated with DC 12V, 10 A. Such a power consumption is very little as compared with the power consumption of a conventional electromagnet type apparatus. A melt of 1 to 10 t can be agitated with a power being increased in accordance with the aforementioned power consumption. Furthermore, as described above, it is necessary to increase the voltage applied in order to increase the agitation speed. Accordingly, it is important for the apparatus that the applied voltage can be varied.

Furthermore, as described above, it is important to increase the number of pairs of electrodes in the magnetic field generating device in order to increase the agitating force. When one pair is used, it takes 1.5 minutes to agitate a predetermined amount of melt in the furnace, but when two pairs are used, it takes 0.8 minutes and when three pairs are used, it takes only 0.3 minutes. Thus, it can be understood that a high-speed agitation can be achieved by increasing the number of pairs.

It can be understood from the aforementioned matters that it is important to determine the applied voltage, the number of poles, the positions of poles, the magnetic field intensity etc. from the purpose of the furnace.

The result of the experiment performed by the present inventor in order to confirm the effects of the embodiments is shown below as Table 1. As can be understood from Table 1, an agitation experiment was performed with respect to aluminum melt and an electrolyte (potassium carbonate $K_2CO_3$ aqueous solution with the weight ratio of 150%) under the shown conditions. As a result, it was possible to confirm the effects of the embodiments of the present invention.

TABLE 1

|  | Electrolyte at 60° C. | | | Aluminum Melt at 700-750° C. | | |
| --- | --- | --- | --- | --- | --- | --- |
| Apparatus | Current A | Voltage V | Flow Rate m/min. | Current A | Voltage V | Flow Rate m/min |
| FIGS. 2 and 3 | 4.5 | 24 | 10-15 | 60-70 | 12 | 5 |
| FIGS. 4 and 5 | 8.5 | 24 | 20-40 | 60-70 | 12 | 5 |
| FIGS. 6 and 7 | 9.0 | 24 | 20-40 | 60-70 | 12 | 5 |
| FIGS. 8 and 9 | 6.1 | 24 | 60-100 | 60-70 | 12 | 150-300 |

The invention claimed is:

1. A melting furnace with an agitator comprising:
a melting furnace comprising a containing space for containing a melt of nonferrous metal;
a magnetic field generating device for causing a magnetic flux to penetrate, from outside, the melting furnace for containing the melt so as to run through the containing space in a direction;
at least one pair of electrode terminals, the electrode terminals facing each other with a predetermined distance in a direction crossing the direction of the magnetic flux at a certain angle, and being capable of connecting to a power supply;
wherein the magnetic field generating device includes a permanent magnet;
the magnetic field generating device is of a monopole type in which one of the north pole and the south pole faces the containing space of the melting surface;
the magnetic field generating device is provided on an outer portion of a furnace bottom of the melting furnace so that the magnet flux from the magnetic field generating device penetrates the melting furnace so as to run through the melt in the furnace in a vertical direction; and;
the electrode terminals constituting the pair face each other substantially in a horizontal direction in the containing space so that a current flows between the pair of electrode terminals through the melt in a horizontal direction;
thereby the melt in the furnace revolves in a clockwise direction or counterclockwise direction around the horizontal line.

2. The melting furnace with an agitator according to claim 1, wherein two or more pairs of electrode terminals are provided.

3. The melting furnace with an agitator according to claim 1, wherein the melting furnace is either in a rectangular container shape or a cylindrical container shape.

4. The melting furnace with an agitator according to claim 1, wherein the cross section of the electrode terminal is in a circular or rectangular shape.

5. The melting furnace with an agitator according to claim 1, further comprising the power supply.

6. The melting furnace with an agitator according to claim 5, wherein the power supply is capable of at least one of switching polarity and adjusting output.

7. A melting furnace with an agitator comprising:
a melting furnace comprising a space for containing a melt of nonferrous metal;
a magnetic field generating device for causing a magnetic flux to penetrate, from outside, the melting furnace for containing the melt to run through the containing space in a direction;
at least one pair of electrode terminals each being capable of connecting to a power supply, the electrode terminals being provided with a predetermined distance therebetween, one of the electrode terminals constituting the pair being provided to a position corresponding to the magnetic field generating device, and the other being provided to an arbitrary position;
wherein the magnetic field generating device is provided on an outer portion of a furnace bottom of the melting furnace;
the magnetic field generating device includes a permanent magnet;
the magnetic field generating device is of a monopole type in which one of the north pole and the south pole faces the containing space of the melting furnace; and
one of the electrode terminals constituting the pair is provided to a position corresponding to the magnetic field generating device at the furnace bottom, and the other is provided to an arbitrary position of a sidewall of the melting furnace, the one of the electrode terminals is connected to one voltage side of a power supply and the other of the electrode terminals is connected to the other voltage side of the power supply.

8. The melting furnace with an agitator according to claim 7, wherein the magnetic field generating device is provided near an outer portion of a furnace bottom of the melting furnace.

9. The melting furnace with an agitator according to claim 7, further comprising a third electrode terminal which is provided to an arbitrary position of a sidewall of the melting furnace so that the third electrode terminal is opposed to the other of the electrode terminals in a horizontal direction, and the third electrode terminal and the other of the electrode terminals are connected to the same voltage side of the power supply.

10. The melting furnace with an agitator according to claim 7, wherein the cross section of one of the electrode terminals is in a circular or rectangular shape, and the cross section of the other of the electrode terminals is in a circular, rectangular, or ring shape.

11. The melting furnace with an agitator according to claim 7, wherein the melting furnace is in a rectangular container shape or a cylindrical container shape.

12. The melting furnace with an agitator according to claim 7, wherein the power supply is capable of at least one of switching polarity and adjusting output.

13. A melting furnace with an agitator comprising:
a melting furnace comprising a containing space for containing a melt of nonferrous metal;
a magnetic field generating device for causing a magnetic flux to penetrate, from outside, the melting furnace for containing the melt so as to run through the containing space in a direction;
at least one pair of electrode terminals, the electrode terminals facing each other with a predetermined distance in a direction crossing the direction of the magnetic flux at a certain angle, and being capable of connecting to a power supply;
wherein the magnetic field generating device includes a permanent magnet;
the magnetic field generating device is of a monopole type in which one of the north pole and the south pole faces the containing space of the melting surface;
the magnetic field generating device is provided on an outer portion of a side surface of the melting furnace so that the magnet flux from the magnetic field generating device penetrates the melting furnace so as to run through the melt in the furnace in a horizontal direction; and
the electrode terminal constituting the pair face each other substantially in a perpendicular direction in the containing space so that a current flows between the pair of electrode terminals through the melt in a vertical direction;
thereby the melt in the furnace revolves in a clockwise direction or counterclockwise direction around the vertical line.

14. The melting furnace with an agitator according to claim 13, wherein the melting furnace is formed to be in a cylindrical container shape, and the magnetic field generating device is provided near an outer portion of a side surface of the melting furnace and is curved along an outer surface of the melting furnace.

* * * * *